United States Patent [19]

Wang

[11] Patent Number: 4,927,908

[45] Date of Patent: May 22, 1990

[54] CURABLE RESIN COMPOSITION COMPRISING CYANATO ARYL SPIRODILACTAM

[75] Inventor: Pen C. Wang, Houston, Tex.

[73] Assignee: Shell Oil Company, Houston, Tex.

[21] Appl. No.: 314,519

[22] Filed: Feb. 23, 1989

[51] Int. Cl.$^5$ .............................................. C08G 69/14
[52] U.S. Cl. .................................... 528/323; 528/170; 528/173; 528/183; 528/190; 528/321; 528/322; 528/423
[58] Field of Search ............... 528/323, 321, 322, 170, 528/173, 183, 190, 423

[56] References Cited

U.S. PATENT DOCUMENTS 4,429,112 1/1984 Gaku et al. .......................... 528/323

Primary Examiner—Harold D. Anderson

[57] ABSTRACT

Novel thermosetting resin compositions comprise (a) a cyanatoaryl-substituted 1,6-diaza[4.4]spirodilactam having cyanatoaryl-containing substituents on each spiro ring nitrogen atom and (b) at least one additional polymerizable monomer having two substituents with multiple bonds between adjacent atoms. The compositions cure upon application of heat to crosslinked resins having good properties.

22 Claims, No Drawings

CURABLE RESIN COMPOSITION COMPRISING CYANATO ARYL SPIRODILACTAM

FIELD OF THE INVENTION

This invention relates to novel thermosetting resin compositions and to cured products obtained by the heating thereof. More particularly, the invention relates to thermosetting resin compositions comprising (a) a cyanato derivative of a hydroxyaryl-substituted 1,6-diaza[4.4]spirodilactam having a hydroxyaryl substituent located on each spiro ring nitrogen atom, and (b) at least one additional polymerizable monomer having at least two functional groups with multiple bonds between adjacent atoms.

BACKGROUND OF THE INVENTION

The curing of monomeric materials to produce thermoset resins is well known in the art. In general, the polymerizable monomers have at least one and customarily more than one reactive group which serves as a site for the curing or crosslinking polymerization to produce the cured products. There are some monomeric materials wherein the active sites are such that the monomer will cure upon application of energy, e.g., heat or high intensity UV light. In many if not most cases, however, a curing agent is necessary to allow the crosslinking reaction to proceed at an acceptable rate. The curing agents are employed in catalytic or stoichiometric amounts relative to the monomer to be crosslinked. The stoichiometric curing agents, i.e., agents which are provided in a substantial quantity relative to the quantity of the monomer, are the more commonly used and are typically multi-functional polymerizable compounds having a plurality of reactive groups capable of participating in crosslinking reactions. A mixture of the monomer and a curing agent, generally referred to as a thermosetting resin composition, is then cured by application of heat, with or without the presence of an accelerator which may be added to obtain a more acceptable rate. Thermosetting resins containing cyanato moieties are known in the art. Poly(cyanato) compounds react with a variety of curing agents to produce thermoset resins having good properties.

Certain of the thermosetting resin compositions have polymerizable monomers which are cyclic in character. The cured products resulting therefrom are often characterized by relatively high glass transition temperatures. Such materials demonstrate dimensional stability in applications where elevated temperatures are likely to be encountered. It would be of advantage to provide a novel class of polycyclic polymerizable monomers which cure by reaction with curing agents to provide cured, crosslinked thermoset products of relatively high glass transition temperature.

SUMMARY OF THE INVENTION

This invention provides novel thermosetting resin compositions comprising a cyanatoaryl-substituted 1,6-diaza[4.4]spirodilactam wherein a cyanatoaryl substituent is located on each of the spiro ring nitrogen atoms, and at least one additional polymerizable monomer of different chemical structure. More particularly, the invention relates to thermosetting resin compositions comprising the cyanatoaryl-substituted spirodilactams and at least one additional polymerizable monomer having at least two functional groups with multiple bonds between adjacent atoms. The invention also provides the crosslinked products obtained by heating thermosetting compositions.

DESCRIPTION OF THE INVENTION

The novel thermosetting resin compositions of the invention comprise 1,6-di(cyanatoaryl-substituted)-1,6-diazaspiro[4.4]nonane-2,7diones and at least one additional polymerizable monomer having at least two functional groups with multiple bonds between adjacent atoms. The spirodilactam portion of the compositions is a 1,6-diaza[4.4]spirodilactam wherein a cyanatoaryl-containing substituent is located on each spiro ring nitrogen atom. Although a wide variety of such substituted spirodilactams having a variety of additional substituents is contemplated by the invention, a preferred class of such spirodilactams comprises spirodilactam derivatives of up to 60 carbon atoms represented by the formula

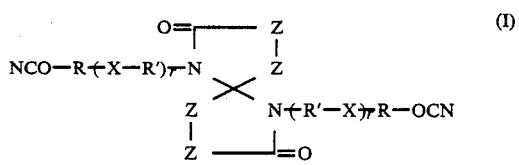

wherein R independently is aromatic of up to 15 carbon atoms and up to 2 aromatic rings, inclusive, R' independently is R or aliphatic of up to 10 carbon atoms inclusive, r independently is 0 or 1, X independently is a direct valence bond, alkylene of up to 8 carbon atoms inclusive, oxy, thio, sulfonyl, carbonyl, dioxyphenylene, i.e.,

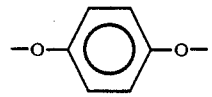

2,2-di(oxyphenyl)propane, i.e.,

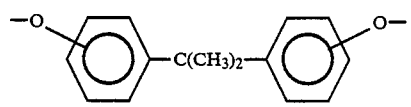

di(oxyphenyl)sulfone

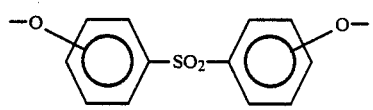

or dioxydiphenylene, i.e.,

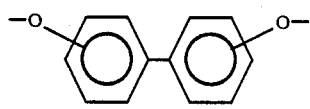

and Z independently is C(Z')$_2$ in which Z' independently is hydrogen, lower alkyl, preferably methyl, halo, preferably the lower halogens fluoro or chloro, or aryl, preferably phenyl, or Z is such that two adjacent Z groups form a ring system Z'' of from 5 to 7 ring atoms up to two of which are heteroatoms selected from nitrogen, oxygen or sulfur with the remainder of the ring atoms being carbon atoms, there being up to 15 carbon atoms in each Z", two of which form a bridge between the carbon atoms connected by the adjacent Z groups. In the above formula I, R and R' independently are hydrocarbyl containing only atoms of carbon and hydrogen or are substituted hydrocarbyl containing additional atoms in the form of inert, carbon atom substituents, e.g., halogen atoms, particularly the middle halogens chloro or bromo. A preferred class of substituted hydrocarbyl R or R' moieties comprises halohydrocarbyl moieties. The group R, and R' when R' is aromatic, includes alkylaromatic and alkenylaromatic and when R' is aliphatic R' includes acyclic aliphatic, cycloaliphatic or arylaliphatic. A preferred R group has a single aromatic ring, i.e., R is phenylene, particularly p- or 1,4-phenylene.

In the embodiment of the above formula I wherein the Z groups are not part of a fused cyclic substituent and are therefore acyclic, i.e., Z is

illustrative cyanatoaryl-substituted spirodilactams are illustrated by 1,6-di(4-cyanatophenyl)-1,6-diazaspiro[4.4]nonane-2,7-dione, 1,6-di(4-cyanato-3-chlorophenyl)-3,8-dimethyl-1,6-diazaspiro[4.4]nonane-2,7-dione, 1,6-di(3 cyanato-5-methylphenyl)-3,4,8,9-tetramethyl-1,6-diazaspiro[4.4]-nonane-2,7-dione, 1,6-bis(4-cyanato-3,5-dibromophenyl)-3-phenyl-1,6-diazaspiro4.4]nonane-Z,7-dione, 1,6-di[4-(3-cyanatobenzoyl)-phenyl]-1,6-diazaspiro[4.4]nonane-Z,7-dione, 1,6-di(4-cyanatophenyl)-3,3,4,4,8,8,9,9-octa-methyl-1,6-diazaspiro[4.4]nonane-Z,7-dione, 1,6-di[4-(4'-cyanatobiphenyl)]1,6-diazaspiro[4.4]nonane-2,7-dione, 1,6-di4-(4-cyanatophenylisopropyl)-phenyl)-3,3-dimethyl-1,6-diazaspiro[4.4]nonane-2,7-dione, 1,6-di[4-(4cyanatophenyloxy)phenyl]-3,8-diphenyl-1,6-diazaspiro[4.4]nonane-2,7-dione and 1,6-di(4-cyanophenyl)-3,4,8,9-tetrafluoro-1,6-diazaspiro[4.4]nonane2,7-dione. In the embodiment of the spirodilactams of formula I wherein the adjacent Z groups of each spiro ring form a fused ring substituent, i.e., adjacent Z groups are Z'", illustrative spirodilactam derivatives include 1,6-di(4-cyanatophenyl)-3,4,8,9-dibenzo-1,6-diazaspiro[4.4]nonane-2,7-dione, 1,6-di[4-(4-cyanato-3-bromophenyloxy)phenyl]-3,4,8,9-di(pyrido)-1,6-diazaspiro[4.4]nonane-2,7-dione and 1,6-di(3-cyanatophenyl)-3,4,8,9-di(cyclo-pentano)-1,6-diazaspiro[4.4]nonane-2,7-dione. Also suitable are those substituted spirodilactams wherein one spiro ring has a fused ring substituent and the other spiro ring is free of fused ring substituents, e.g., 1,6-di[4-(4-cyanatophenylthio)phenyl]-3,4-benzo-1,6-diazaspiro[4.4]nonane- 2,7-dione and 1,6-di[1-(4-cyanatonaphthyl)]-3,4-cyclo(4-hexeno)-1,6-diazaspiro[4.4]nonane-2,7-dione.

The cyanatoaryl-substituted spirodilactams of the above formula I wherein R and R' are aromatic and hydrocarbyl are preferred and further preference is given to such spirodilactams wherein r is 0 and R is a single aromatic ring. Within the spirodilactam ring portion of the molecule, spirodilactams free from fused ring substituents are preferred as are the spirodilactams wherein both spiro rings incorporate a fused ring suhstituent. The compound 1,6-di(4-cyanatopheny'l)-1,6-diazaspiro[4.4]nonane2,7-dione is an especially preferred member of the former class whereas 1,6-di(4-cyanatophenyl)-3,4,8,9-dibenzo-1,6-diazaspiro[4.4]nonane-2,7-dione is an especially preferred member of the latter class.

The cyanatoaryl-substituted spirodilactams of formula 1 are produced by reaction of a cyanogen halide with the corresponding hydroxyaryl-substituted spirodilactam in the presence of a tertiary amine. In terms of the cyanatoaryl-substituted spirodilactams of formula 1, the hydroxyaryl precursors are represented by the formula

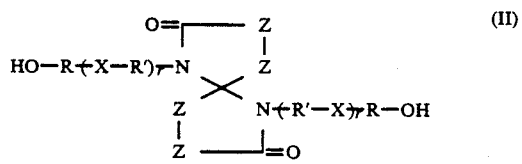

wherein R, R', r, X and Z have the previously stated meanings. The hydroxyaryl-substituted spirodilactams and methods for their production are described in more detail and claimed in copending U.S. patent applications Ser. No. 172,000 filed Mar. 23, 1988, Ser. No. 172,052, filed Mar. 23, 988 and Ser. No. 245,618 filed Sept. 16, 1988, each of which is incorporated by reference. A special class of such spirodilactams having 1-alkenyl substituents on aromatic carbon atoms ortho to the hydroxyl group of the hydroxyaryl substitutent is described and claimed in copending U.S. patent application Ser. No. 314,520 filed Feb. 23, 1989, incorporated herein by reference.

The general procedure for the production of the hydroxyarylsubstituted spirodilactams of the above formula II is the reaction of a hydroxy-containing primary amino compound with a spriodilactam precursor selected from 4-oxoheptanedioic acid compounds or 1,6-dioxo[4.4]spirodilactones. In terms of the hydroxyary)-substituted spirodilactams of formula II, the hydroxy-containing primary amino compound is represented by the formula

wherein R, R' X and r have the previously stated meanings. Also in terms of the spirodilactams of formula II, the 4-oxoheptanedioic acid compounds are represented by the formula

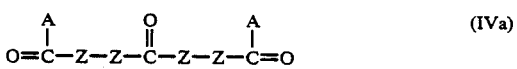

wherein Z has the previously stated meaning and A is hydroxy, lower alkoxy or halo. The spirodilactones utilized as the spirodilactam precursor are represented by the formula

wherein Z has the previously stated meaning.

The hydroxy-containing primary amino compound and the spirodilactam precursor are typically contacted in a molar ratio of about 2:1 in the presence of an inert reaction diluent capable of dissolving at least a portion of each reactant at reaction temperature. A preferred class of reaction diluents comprises N-alkylamides such as N,N-dimethylacetamide or N-methyl-2-pyrrolidone. Reaction conditions include a reaction temperature from about 80° C. to about 200° C. and a reaction pressure sufficient to maintain the reaction mixture in the liquid phase. Such pressures are from about 0.8 atmosphere to about 20 atmospheres. Subsequent to reaction, the hydroxyaryl-substituted spirodilactam is recovered, if desired, by conventional methods such as extraction, solvent removal and precipitation. The isolation of the hydroxyaryl-substituted spirodilactam is not required, however, and the spirodilactam is further reacted in situ to form the cyanato derivative without isolation. By way of specific illustration, p-aminophenol reacts with either 4-oxoheptanedioic acid or 1,6-dioxaspiro[4.4]nonane-2,7-dione to produce 1,6-di(4-hydroxyphenyl)-1,6-diasaspiro[4.4]nonane-2,7-dione and 4-amino-4'-hydroxybiphenyl reacts with either di(2-carboxyphenyl)ketone or 3,4,8,9-dibenzo-1,6-dioxaspiro[4.4]nonane-2,7-dione to produce 1,6-di[4-(4'-hydroxybiphenyl)]-3,4,8,9-dibenzo-1,6diasaspiro[4.4]nonane-2,7-dione.

A somewhat special case exists when the hydroxyaryl-substituted spirodilactam has a 2-alkenyl, e.g., allyl, substituent on an aromatic carbon atom ortho to the hydroxyl group of the hydroxyaryl substituent. Although such ortho-alkenyl hydroxyaryl-substituted spirodilactams are suitably produced by the above process, they are more conveniently produced by conversion of the hydroxyaryl-substituted spirodilactam to the corresponding alkali metal salt and reaction of that salt with 2-alkenyl halide, e.g., allyl bromide, to produce the corresponding 2-alkenyl ether of the hydroxyaryl-substituted spirodilactam by methods conventional for the production of allyl-type ethers of bisphenols. The 2-alkenyl ethers are then subjected to the well-known Claisen Rearrangement to produce the ortho-2-alkenyl hydroxyaryl-substituted spirodilactam. The 2-alkenyl ethers are the subject of copending U.S. patent application Ser. No. 245,433 filed Sept. 16, 1988 now U.S. Pat. No. 4,847,338 and the ortho-alkenyl hydroxyaryl-substituted spirodilactams are the subject of copending U.S. patent application Ser. No. 314,520 filed Feb. 23, 1989, each of which is incorporated herein by reference.

The production of cyanato derivatives of the hydroxyaryl-substituted spirodilactams is by reaction with a cyanogen halide, preferably cyanogen chloride or cyanogen bromide, more preferably cyanogen bromide. The reaction takes place in the liquid phase in the presence of a tertiary amine employed to react with the hydrogen halide by-product and facilitat its removal from the reaction mixture through formation of a quaternary ammonium salt. Trialkyl amines are satisfactory for this purpose, for example, triethylamine. The cyanogen halide and the spirodilactam are usually provided in a molar ratio of about 2:1 in a diluent such as an N-alkylamide. Typical reaction temperatures are from about 10° C. to about 15° C. at a reaction pressure sufficient to maintain the mixture in the liquid phase at reaction temperature. Such pressures are generally from about 0.8 atmosphere to about 10 atmospheres. Subsequent to reaction the cyanatoaryl-substituted spirodilactam, e.g., the compounds of formula I, are recovered by conventional methods including the removal of the quaternary ammonium salt co-produced as by filtration or decantation and separation of the spirodilactam derivative as by extraction or precipitation with a nonsolvent. The cyanatoaryl-substituted spirodilactams as well as self-cured products resulting therefrom are the subject of copending U.S. patent application Ser. No. 314,518, filed Feb. 23, 1989. Such self-cured products are obtained by heating the cyanatoaryl-substituted spirodilactam, generally a low melting solid, to a temperature above about 150° C.

The thermosetting resin compositions of the invention comprise the cyanatoaryl-substituted spirodilactams of formula I and at least one additional monomer having at least two substituents with multiple bonds, i.e., more than a single valence bond, between adjacent atoms. Although the precise nature of the interaction between the cyanato derivatives and the additional polymerizable monomers that takes place during the curing of the thermosetting resin composition is not known with certainty, it is considered likely that the multiple bonds of the cyanato groups react with the multiple bonds of the other polymerizable monomers.

The additional polymerizable monomers of the thermosetting resin composition suitably have a variety of functional substituents having multiple bonds between adjacent atoms. The substituents are hydrocarbyl with multiple bonds between adjacent carbon atoms or are non-hydrocarbyl with multiple bonds between adjacent atoms at least one of which is not carbon. Illustrative of such substituents are hydrocarbyl substituents such as vinyl, allyl, propargyl and styrylmethyl and non-hydrocarbyl substituents such as cyanato and maleimido.

The structure of the additional polymerizable monomer to which the substituents are attached is not critical provided that it is inert under the conditions at which the thermosetting resin compositions are cured and not unduly sterically hindered. A variety of organic linking groups which meet these criteria are suitably found in the additional polymerizable monomers. In the preferred embodiments of the invention, the moieties which link the reactive substituents are represented by the group L wherein L is isocyanurate or —R—X—(R-)$_r$— wherein R, X and r have the previously stated meanings. Expressed differently, the additional polymerizable monomers are represented by the formula L(Sub)$_v$  (V)

wherein L has the previously stated meaning, v is an integer of at least 2 and is the valance of the linking group L and Sub represents a substituent having multiple bonds between adjacent atoms. Preferred Sub groups are alkenyl, preferably allyl, alkynyl, preferably propargyl, vinylaromaticmethyl, preferably styrylmethyl, cyanato and maleimido. Illustrative of the additional polymerizable monomers are 1,9-decadiene, 2,2-di(4-allyloxyphenyl)propane, di(3-cyanatophenyl)methane, 1,5-di(cyanato)naphthalene, 4,4'-di(maleimido)-biphenyl, 1,3-di(propargyl)benzene, di(4-maleimidophenyl)sulfone, 1-allyl-4-styrylmethylbenzene, 2,2-di(4-cyanatophenyl)propane, 1,3-di(4-cyanatophenyl)propane, triallylisocyanurate di(4-maleimidophenyl)methane and divinylbenzene.

The thermosetting resin compositions of the invention are the cyanatoaryl-substituted spirodilactam and at least on additional polymerizable monomer as described above. The compositions are usefully the spirodilactam plus three or even more additional polymerizable monomers but preferably the compositions comprise the spirodilactam plus from one to two additional polymerizable monomers. The precise proportions of the components in the compositions of the invention are not critical and each component is suitably present in a quantity of from about 1% by weight to about 99% by weight based on the total composition. In the preferred embodiments the cyanatoaryl-substituted spirodilactam is present in at least about 40% by weight based on total composition with the additional polymerizable monomer(s) being present in a total of no more than about 60% by weight on the same basis. In even more preferred thermosetting resin compositions, the substituted spirodilactam is present in a quantity of about 50% by weight based on total composition, with one additional polymerizable monomer being present in at least about 40% by weight on the same basis and with any additional polymerizable monomer being present as the remainder of the composition.

The thermosetting resin compositions of the invention are produced by forming an intimate mixture of the cyanatoaryl-substituted spirodilactam and the additional polymerizable monomer(s). The method of mixing is not critical and conventional methods of stirring, blending or co-melting are satisfactory provided that the mixing does not result in sufficient heat or energy to cause the cure or crosslinking of the composition.

The curing or crosslinking of the thermosetting resin compositions of the invention is effected by the application of heat. The curing or crosslinking usually results from heating the mixture to a temperature of at least about 150° C. but preferably to a temperature from about 175° C. to about 300° C. It is often desirable to effect the curing by heating in stages. For example, the composition is heated to a relatively low curing temperature, e.g., from about 175° C. to about 210° C., for a time sufficient to initiate the curing process and then maintained at a higher curing temperature, e.g., from about 215° C. to about 275° C. to complete the cure. The cured Products are highly crosslinked solids having relatively high glass transition temperatures and good properties of rigidity, strength and solvent resistance. The compositions are processed by methods which are conventional for the curing of thermosetting resin compositions to produce cured products which are useful in adhesive compositions and in coating and structural applications in the aerospace and electronic industries.

The invention is further illustrated by the following Illustrative Embodiments which should not be regarded as limiting the invention.

ILLUSTRATIVE EMBODIMENT I

The compound, 1,6-di(4-hydroxy-3-allylphenyl)-1,6-diazaspiro4.4]nonane-2,7-dione, is produced by converting the sodium salt of 1,6di(4-hydroxyphenyl)-1,6-diazaspiro[4.4]nonane-2,7-dione to the corresponding di(allyl) ether through reaction with allyl chloride by conventional methods. The 1,6-di(4-allyloxyphenyl)-1,6-diazaspiro4.4]nonane-2,7-dione was then subjected to a Claisen Rearrangement by heating to about 200° C. The ortho-allyl hydroxy compound was then contacted at about 0° C. in the presence of a slight stoichiometric excess of cyanogen bromide and triethylamine. When reaction was complete, triethylammonium bromide was removed by filtration and 1,6-di(4-cyanato-3-allylphenyl)-1,6-diazaspiro[4.4]nonane-2,7-dione was precipitated by mixing with ether-hexane.

ILLUSTRATIVE EMBODIMENT II

A mixture of equal portions by weight of the product of Illustrative Embodiment I and di(4-maleimidophenyl)methane was melted at 130°–150° C. The mixture is then heated in an oven, in a first stage at 200° C. for 2 hours and in a second stage at 220° C. for an additional 6 hours. The resulting product is a hard, insoluble, crosslinked resin having a glass transition temperature in excess of 300° C.

ILLUSTRATIVE EMBODIMENT III

A mixture of equal parts by weight of the product of Illustrative Embodiment I and 2,2-bis(4-cyanatophenyl)propane was melted at 100°–120° C. The resulting mixture was heated in an oven, initially at 200° C. for 2 hours and then at 220° C. for an additional 4 hours. The resulting product was a hard, insoluble, crosslinked product having a glass transition temperature 216° C.

What is claimed is:

1. A curable thermosetting resin composition comprising (a) a cyanatoaryl-substituted 1,6-diaza[4.4]-spirodilactam having a cyanatoaryl-containing substituent on each spiro ring nitrogen atom and (b) at least one additional polymerizable monomer of up to 30 carbon atoms inclusive having at least two functional substituents in the molecule with multiple bonds between adjacent atoms.

2. The composition of claim 1 wherein the cyanatoaryl-substituted spirodilactam is a spirodilactam derivative of up to 60 carbon atoms represented by the formula

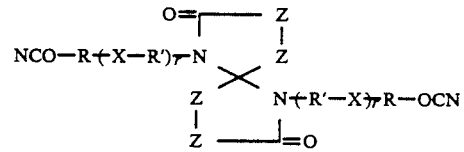

wherein R is aromatic of up to 15 carbon atoms and up to two aromatic rings inclusive, R' is R or aliphatic of up to 10 carbon atoms inclusive, r is 0 oX is a direct valence bond or x represents oxo, thio, sulfonyl, carbonyl, dioxyphenylene, 2,2-di(oxyphenyl)propane, di(oxyphenyl)sulfone or dioxyphenylene, and Z independently is

in which Z' is hydrogen, lower alkyl, lower halo or phenyl, or Z is such that two adjacent Z groups taken together form a ring system Z" of from 5 to 7 ring atoms, up to two of which are heteroatoms selected from nitrogen, oxygen or sulfur with the remainder of the ring atoms being carbon atoms, there being up to 15 carbon atoms in each Z', two of which form a bridge between the carbon atoms connected by the adjacent Z groups.

3. The composition of claim 2 wherein at least one additional polymerizable monomer is represented by the formula L(Sub)$_y$ wherein L is a linking group selected from isocyanurate or —R—X—R,— wherein R, X and r have the previously stated meanings, v is an integer of at least 2 and Sub is a substituent having multiple bonds between adjacent carbon atoms.

4. The composition of claim 3 wherein Sub is selected from alkenyl, alkynyl, vinylaromaticmethyl, cyano or maleimido.

5. The composition of claim 4 wherein R is phenylene.

6. The composition of claim 5 wherein the substituted spirodilactam is present in at least 40% by weight based on total composition.

7. The composition of claim 6 wherein, within the substituted spirodilactam, each r is 0.

8. The composition of claim 7 wherein Sub is allyl.

9. The composition of claim 7 wherein Sub is cyanato.

10. The composition of claim 7 wherein Sub is maleimido.

11. The composition of claim 7 wherein each Z is

12. The composition of claim 11 wherein Z' is hydrogen.

13. The composition of claim 12 wherein each R is p-phenylene.

14. The composition of claim 13 wherein L is —R—R,—.

15. The composition of claim 14 wherein Sub is maleimido.

16. The composition of claim 15 wherein at least one additional polymerizable monomer is di(4-maleimidophenyl)methane.

17. The composition of claim 7 wherein adjacent Z groups are Z".

18. The composition of claim 16 wherein Z" is benzo.

19. The composition of claim 17 wherein, within the substituted spirodilactam, R is p-phenylene.

20. The composition of claim 18 wherein L is —R—X—R,— and Sub is allyl, propargyl, styrylmethyl, cyanato or maleimido.

21. The crosslinked insoluble product obtained by heating the composition of claim 1 to a temperature above 150° C.

22. The crosslinked insoluble product obtained by heating the composition of claim 15 to a temperature above 150° C.

* * * * *